United States Patent [19]
Gamble et al.

[11] Patent Number: 4,783,220
[45] Date of Patent: Nov. 8, 1988

[54] VESICLE INK COMPOSITIONS

[75] Inventors: Ronald C. Gamble, Pasadena, Calif.; Micheal C. Hair, Oakville, Canada; Sava R. Lukac, Toronto, Canada; Michael G. Taylor, Mississauga, Canada

[73] Assignees: Xerox Corporation, Stamford, Conn.; Vestar, Inc., Pasadena, Calif. ; part interest to each

[21] Appl. No.: 944,675

[22] Filed: Dec. 18, 1986

[51] Int. Cl.$^4$ ............................................. C09D 11/06
[52] U.S. Cl. ........................................ 106/27; 106/22; 106/28; 106/266
[58] Field of Search ...................... 106/22, 27, 28, 122, 106/243, 244, 266

[56] References Cited

U.S. PATENT DOCUMENTS

| | | | |
|---|---|---|---|
| 3,471,415 | 10/1969 | Friedman et al. | 252/62.54 |
| 3,533,727 | 10/1970 | Grunwald et al. | 8/513 |
| 3,928,226 | 12/1975 | McDonough et al. | 106/21 |
| 4,314,259 | 2/1982 | Cairns et al. | 346/75 |
| 4,409,039 | 10/1983 | Lepesant et al. | 106/22 |

FOREIGN PATENT DOCUMENTS 50-34974 11/1975 Japan .
58-89668 5/1983 Japan .

OTHER PUBLICATIONS

Z. Kovac and C. Sambucetti, *Magnetic Ink for Magnetic Ink Jet Printing*, Colloids and Surfaces in Reprographic Technology, 1982.

J. Israelachvili et al, *Theory of Self-Assembly of Hydrocarbon Amphiphiles into Micelles & Bilayers*, J. Chem. Soc., Faraday Trans. 2, 1976, 72, 1525.

D. Evans et al., *Molecular Forces in the Self-Organization of Amphiphiles*, J. Phy. Chem., 1986, 90, 226–234.

*Liposome Technology*, Preparation of Liposomes, vol. I, Gregoriadis (Ed.), CRC Press, Inc. (1984).

Primary Examiner—Amelia B. Yarbrough
Attorney, Agent, or Firm—Lyon & Lyon

[57] ABSTRACT

Ink compositions consisting of small unilamellar or multilamellar vesicles formed from surfactants of anionic, cationic, zwitterionic and nonionic molecules having an oil soluble dye, inclusive of a lipid-soluble dye associated therewith are described. The dye to surfactant ratio is preferably from about 1:1 to about 1:10. The compositions are useful in traditional printing techniques such as flexography and rotogravure and in electronic printing systems such as with an ink-jet printer.

38 Claims, 1 Drawing Sheet

SINGLE UNILAMELLAR SYSTEM

TYPICAL VESICLE FORMING AMPHIPHILIC MOLECULE

BILAYER

SINGLE UNIMELLAR SYSTEM

VESICLE INK COMPOSITIONS

FIELD OF INVENTION

This invention relates generally to ink compositions and more particularly to ink compositions comprised of vesicles.

One embodiment of the present invention is directed to ink compositions comprised of vesicles formulated from, for example, surfactants with a polar group containing two hydrocarbon tails. Therefore, there can be selected for the ink compositions of the present invention, vesicles generated from molecules that form anionic, cationic, nonionic, and zwitterionic components. Vesicles useful in the present invention thus include phospholipid vesicles inclusive of single unilamellar and multilamellar vesicles having a dye associated therewith. Ink compositions comprised of the aforementioned vesicles are useful in printing systems, particularly ink jet printing and possess the desirable characteristics indicated hereinafter including excellent waterfastness and storage stability.

BACKGROUND OF THE INVENTION

With the rapid advancement of computer technology, there has been a concomitant development of improved printing technologies. In addition to printing methods such as letterpress, offset, lithography, flexography and rotogravure, advanced electronic printing systems have emerged. In electronic printing systems, information is transmitted from a computer to a printing instrument in digital form. This format allows for the use of more sophisticated printing devices than the traditional formed character impact system such as the "daisy wheel" printer. Examples of such non-impact printing technologies currently in use or development are: laser xerography, thermal, thermal transfer, electrostatic and ink jet. These methods form printed images by "bit-mapping" wherein the image is formed by discrete dots separately addressable so that text and graphical information can be intermixed in a single printed document. Since these methods do not rely on the impact between a character forming element and an inking ribbon, they can operate more quietly and at a higher speed than former printing methods.

Printing systems, in particular non-impact electronic technologies, necessitate appropriate materials such as papers and ink compositions to produce a high quality product. One type of modern electronic printing instrument is the ink jet printer. Ink jet printers include continuous and so-called "drop-on-demand" ink-jet systems, both of which emit droplets of ink under pressure from a nozzle. In the continuous jet systems, ink is ejected in a continuous stream, and the ink that is not used for printing is recirculated. In this system, an electro-mechanical transducer vibrates to break up the steady flow of ink into droplets which are electrically charged and correspond in amount to the signal strengths for the shape of the characters. Drop-on-demand ink jet systems do not recycle ink and rely on piezo-crystal formation to generate a spurt of high pressure to force out drops of ink onto the paper. The bubble-jet system, typified by the Hewlett Packard "Thinkjet ®" printer, is a variation of the drop-on-demand system, where heat is used to generate bubbles that create a brief pulse of high pressure that propels ink out of a chamber onto the paper. For printing purposes, it is necessary that drops be uniform in size, equally spaced from each other, and be formed at a high rate. Z. Kovac and C. Sambucetti, *Magnetic Ink for Magnetic Ink Jet Printing*, Colloids and Surfaces in Reprographic Technology, 1982, the disclosure of which is incorporated herein by reference.

In the past, the driving method and structure of the printing head in ink jet printers have caused difficulties in achieving acceptable results (U.S. Pat. No. 4,314,259) and have limited the type of ink formulations which will work properly. Optimal print quality is a function of the physical properties of the ink composition such as surface tension and viscosity. Ink jet printer inks are typically formed by dissolving or dispersing dyes or pigments in solvent with additives such as antiseptics and stabilizers. Technical problems encountered with these solvent-based inks include those due to interactions between the ink and the paper surface: after striking the paper, the solvent used in the ink drop spreads before drying. Dye dissolved in the solvent spreads along with the solvent, resulting in a "feathering" effect which degrades resolution since adjacent dots of ink may overlap. Moreover, the dyes in the ink may separate chromatographically in this process, causing an undesirable effect. The solvent and dye also tend to penetrate into the paper. This can result in "print through", where a shadow of the image is observed on the reverse side of the paper sheet. Two-sided printing is not possible under these circumstances.

Previously, the above problems have been treated by modifying the surface of the paper. Typically, the paper used in ink jet printing is heavily coated with a variety of materials such as clays designed to reduce or control the spreading of the ink. These coatings, however, increase the cost of the paper and often reduce its aesthetic appeal. In addition, coatings which work well with a particular ink jet may not perform well with other marking instruments used in printing apparatus, such as pens or pencils. Alternatively, particulate inks have been used to eliminate feathering, but have been found to settle out of the ink solution over a long period of time and tend to clog the printer nozzle.

In general therefore, there is a need for new and improved ink compositions. Specifically, there is a need for improved ink compositions enabling images to be found that have excellent resolution and improved waterfastness and lightfastness. Water-fastness can be defined as that property of the ink composition which renders it resistant to removal or spreading on the paper when exposed to water after image formation. Lightfastness can be defined as that property of the ink composition which renders it resistant to a change in color when exposed to the light. Improved lightfastness is obtained with the ink composition of the present invention primarily because of the presence of an oil soluble dye.

Additionally, there is a need for ink compositions wherein the compositions are storage stable, i.e. the dyes selected are permanently retained within the vesicle and do not settle out on storage.

There is also a need for black and colored ink jet compositions with vesicles therein which can be selected for the development of images of excellent resolution on plain uncoated papers.

Moreover, there is a need for ink compositions that exhibit a high optical density which provides a measure of the quality of the appearance of the ink on paper. A reflectance (optical density) in the range of 1.0 to 1.4 is preferred. An ink composition should contain a dye content in the range of about 3-7% of the total ink composition depending on the molar extinction coefficient and molecular weight of the dye. The preferred viscosity range is low, between about 1.5 and 1.8 cps (measured against water with a value of 1) for ink jet printers using a piezo-electric driver and 2-3 cps for bubble jet printers. The preferred surface tension is approximately 55-60 dynes/cm.

In addition, other important qualities possessed by the ink compositions of the present invention include relative fast drying on the paper (within a few seconds) and water resistance after drying. Successful ink compositions are also chemically stable and have minimal settling out of particles for longer shelf-life, for example 1-2 years. If used in a bubble jet printer, the ink will be subjected to 300° C. (bulk temperature approaches 100° C.) and must be able to retain the qualities described above under these conditions. Finally, the ink must be safe, i.e., contain an approved dye or pigment, and should use relatively inexpensive materials and be easy to manufacture.

These characteristics, particularly the low viscosity and the water base make these ink compositions also suitable for flexographic and rotogravure printing methods. Flexography uses a single roller which achieves more controlled inking than offset and prints with a soft, shallow relief plate enabling printing on flexible materials.

The flexographic process requires solvents that do not erode rubber rollers and printing plates, thus making the water-based ink composition of the present invention ideal for this process. Further advantages of water inks in the flexographic and rotogravure processes include excellent press stability, printing quality, heat resistance, absence of fire hazard associated with solvents, and the convenience and economy of water.

SUMMARY OF THE INVENTION

It is an object of the present invention, therefore, to provide a high quality, effective ink composition comprised of vesicles and possessing the desired characteristics indicated above for use in printing systems including those incorporating electronics as well as traditional flexographic and rotogravure printing methods.

Another object of the present invention is the provision of ink compositions that can be black or another color and which is comprised of vesicles.

Further, in another object of the present invention there are provided vesicle ink compositions which enable images of superior resolution.

It is an additional object of the invention to provide water-based ink compositions containing small particles which will not clog inkjet printing systems, are storage stable, and which possess additional characteristics suitable for use in modern printing technologies such as high optical density and water resistance, and which also reduce the costs associated with printing.

The foregoing difficulties of using solvent-based inks are eliminated by the water-based colored or black ink compositions according to the present invention which comprise vesicles, inclusive of unilamellar and multilamellar vesicles having oil soluble dyes, inclusive of lipid-soluble dyes, associated therewith. In one specific embodiment of the present invention, the ink compositions are comprised of from about 70 percent to about 95 percent by weight of water; from about 5 percent to about 30 percent by weight of lipid or other amphiphilic material and dye components. In an embodiment of the present invention, the inks are comprised of from about 70 percent to about 95 percent by weight of water; from about 5 percent by weight to about 30 percent by weight of a phospholipid in the form of unilamellar vesicles and associated therewith an oil soluble dye, inclusive of lipid soluble dyes, present in an amount of from about 1.0 percent to about 10 percent by weight, and wherein the vesicles of the resulting inks are preferably of a diameter of from about 100 nanometers to about 400 nanometers. Generally, ink compositions of this embodiment may be prepared by suspending a phospholipid, an antioxidant and a microbial inhibitor in water, subjecting the suspension to a shear force sufficient to generate vesicles of desired size, for example by sonication, adding lipid soluble dye, adjusting the pH of the solution to enhance the incorporation of dye into the lipid vesicles, further subjecting it to sufficient shear force, and then centrifuging and decanting the solution to obtain an ink composition of dye-associated phospholipid vesicles that are from approximately 40-800 nanometers in diameter.

In a second embodiment of the present invention, the phospholipid is replaced by dioctadecyl dimethyl ammonium bromide but the ink and its preparation are otherwise the same as described above.

DETAILED DESCRIPTION

The ink composition of this invention comprises dye molecules which are soluble in the hydrocarbon bilayer of vesicles formed from surfactants selected from the group consisting of anionic, cationic, zwitterionic and nonionic molecules. The dye molecules are associated with small (about 40-800 nanometers in diameter, preferably about 100 to about 400 nanometers) vesicles, in the form of single unilamellar and multilamellar vesicles. Formation of vesicles by the dispersion of amphiphilic compounds in water is fully described in J. Israelachvili, D. Mitchell and B. Ninham, *Theory of Self-Assembly of Hydrocarbon Amphiphiles into Micelles and Bilayers*, 1976 and D. Evans and B. Ninham, *Molecular Forces in the Self-Organization of Amphiphiles*, J. Phys Chem., 1986, 90, 226-34, the disclosures of which are incorporated herein by reference. The amphiphiles are molecules with polar and non-polar molecular regions. When dispersed in water, the polar regions are readily solvated while the non-polar fragments of the amphiphile are poorly solvated. Above the critical micelle concentration (CMC), the amphiphiles spontaneously self-assemble to form a variety of mesophases. The CMC is reached when the concentration of the surfactant solute in the bulk of the solution exceeds a limiting value. There is a decrease in the overall free energy of the system due to the desolvation of the head groups and the hydrophobic interaction of the hydrocarbon chains which provides the driving force for aggregation. Such vesicles formed by the dispersion of amphiphilic compounds in water are known in the art and may be prepared, for example, using sonication as described in *Liposome Technology*, Preparation of Liposomes, Vol. I, Gregoriadis (Ed.), CRC Press, Inc.

(1984), or by homogenization by the invention disclosed in copending application, Ser. No. 696,727, filed Jan. 31, 1985 for "METHOD FOR PREPARING SMALL VESICLES USING MICROEMULSIFICATION," the disclosures of which are incorporated herein by reference with the modifications set forth herein. Such preparation methods subject the suspension to a high shear force sufficient to generate vesicles of the desired size. These vesicles are capable of solubilizing non-polar dyes, yielding an aqueous-based ink.

Figure 1:
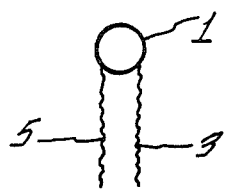
FIG. 1 graphically illustrates a typical vesicle-forming amphiphilic molecule.
Figure 2:
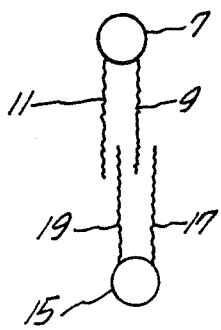
FIG. 2 graphically illustrates a bilayer.
Figure 3:
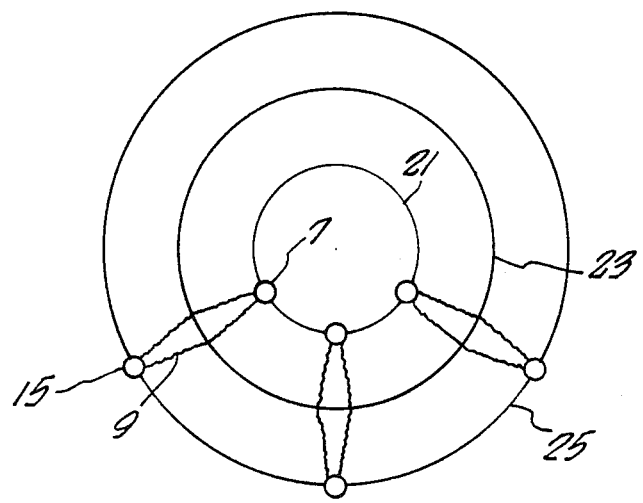
FIG. 3 graphically illustrates a single unimellar system.

A typical amphiphilic molecule from which vesicles are formed illustrated in FIG. 1 includes a polar head group 1 and two long chain nonpolar hydrocarbon moieties 3 and 5. The bilayer structure shown in FIG. 2 includes polar head groups 7 and 15 and nonpolar hydrocarbon moieties 9, 11 and 17, 19 respectively. The single unilamellar system shown in FIG. 3, produced by sonication of the mesophases comprises polar head groups 7, 15, nonpolar hydrocarbon tail 9, an inside polar layer 21, a hydrocarbon segment 23 and an outside polar layer 25.

In general, because of geometric constraints, vesicles are formed from molecules which contain two long hydrophic chains attached to the same hydrophobic head group. Classes of vesicles thus include those formulated from anionic, cationic, non-ionic and zwitterionic head groups. Specific examples include dihexadecyl phosphate (anionic), dioctadecyl dimethyl ammonium bromide (cationic), diacyl glycerides and their ethoxylated derivatives (non-ionic) and phospholipids (zwitterionic).

In the preferred embodiment, the phospholipid of the vesicles is preferably partially purified (greater than 70% pure) phospholipid, which is less expensive than pure phospholipid and thus decreases the costs of preparing the ink composition, although substantially pure phospholipids may, of course, also be used. One such phospholipid is soybean L-α-lecithin. Egg lecithin (phosphatidylcholine) may also be used.

The general formulation of this embodiment of the ink composition of the present invention is phospholipid comprising about 5% to about 30% and preferably about 5% to 20% by weight of the total ink composition in an aqueous medium such as distilled water. The dye to phospholipid ratio is between about 1:1 to 1:10 by weight. To the aqueous medium, there may be added about 0 to about 0.4% by weight of an antioxidant, and about 0 to about 0.05% by weight of a microbial inhibitor. A preferred antioxidant is L-ascorbic acid, although vitamin E or other antioxidants such as eugenol or ionol may also be used. A preferred microbial inhibitor is sodium azide. Further other additives can be incorporated into the inks if needed, such as humectants and the like.

Illustrative examples of oil-soluble dyes, inclusive of lipid-soluble dyes, that may be used in the present invention include Giemsa (May-Greenwald's) stain or Sudan Black, commercially available from Fisher, Inc. or Eastman Kodak, Rochester N.Y.; Sudan I, and nigrosine commercially available from Aldrich Chemical; Sudan II commercially available from Aldrich Chemical; and other classes of dyes such as Yellow Dyes commercially available from Pylam, Inc. (Garden City, N.J.); Neozapan Red GE available from BASF Chemical Company; Oil Blue A dyes commercially available from E.I. DuPont; Methyl Violet 1 B commercially available from Aldrich Chemical; Sudan Red BB commercially available from BASF Chemical Company; Sudan Orange G; Oil Red O; para-phenylazophenol; Rose Bengal, and 4′,5′-dibromofluoroscein, all commercially available from Aldrich Chemical; Sudan Red 7B; Sudan Black B; Sudan Yellow 146; Neozapan Blue; Oracet Yellow GN, available from Ciba-Geigy; BASF Sudan Yellow 150; BASF Sudan Red 7B; Oil Yellow; Bayer Ceres Red 3R; Orient Chemical Ind., Ltd.; Oil Pink 312; Pylam Pylakrome Pink LX 1900; Bayer Ceres Blue R; BASF Neozapan 807; BASF Sudan Deep Black; Bayer Ceres Black BN; and the like. Lipid soluble dye molecules typically have a large hydrophobic portion and a smaller hydrophilic region depending on the type of dye. It is believed that the ink molecule partitions into the bilayered membrane structure of the vesicle (FIG. 2) during formation of the composition such that the hydrophilic region of the dye molecule is exposed to water, and the hydrophobic region resides within the hydrocarbon portion of the vesicle membrane. The hydrophilic nature of the dye molecule is due in part to the presence of an electric charge generated by protonation or deprotonation of a chemical group in the hydrophilic region of the molecule. This charge may be created or amplified by alterations in the acidity (pH) of the region. Thus, manipulations of pH may enhance the incorporation of dye into the vesicles of the ink composition of the invention. The optimal pH for incorporating dye may vary over a wide range from a pH of about 2 to a pH of about 10 depending on the specific dye. For example, the optimum pH for incorporating May-Greenwald's dye in lecithin is approximately 2. In addition, temperature during preparation of the composition may affect dye incorporation. Dye uptake into the ink may range from about 1.0 percent by weight/ml of ink composition to about 10 percent.

A preferred method of preparing the ink composition of this invention essentially comprises suspending about 5 g of the surfactant, and optionally about 0 to about 0.4% by weight antioxidant and about 0 to about 0.05% by weight microbial inhibitor in about 20 to about 25 milliliters water, and sonicating the suspension for 3 minutes at low power (approximately 100 micron peak-to-peak excursion at 20 $KH_z$). From about 0.5 g to about 5 g lipid soluble dye is then added for a dye to phospholipid ratio between 1:1 to 1:10 by weight and the suspension is sonicated at high power (approximately 300 micron peak-to-peak excursion at 20 $KH_z$ to form dye-associated vesicles that are approximately 40 to 800 nanometers in diameter. The solution is then centrifuged (2400 r.p.m., 12 inch rotor) for approximately ten minutes and decanted, yielding the ink composition which comprises a dye soluble in the hydrocarbon bilayer of vesicles formed from surfactants selected from the group consisting of anionic, cationic, zwitterionic, and nonionic molecules. No organic solvent is used.

The following examples are presented to illustrate the invention, and are not intended to limit the scope thereof.

VESICLE INK FORMULATIONS

Example I

The following procedure was used to prepare violet colored ink. Five (5) grams of 70% pure soybean L-α-lecithin (Calbiochem, La Jolla, Calif.) were added to 25 milliliters distilled water in a roundbottomed flask which contained 20 milligrams of L-ascorbic acid (sodium salt) and 20 milligrams of 0.2% sodium azide. The mixture was dispersed using a heat system model W-

225R (Heat Systems, Farmingdale, N.Y.) sonicator equipped with a microtip, No. 4 setting (approximately 190 micron peak-to-peak excursion at 20 KHz). After about five minutes of sonication, drops of 6N HCl were added, which dropped the pH to 4.2 from about 6.5, and the mixture was sonicated for another five minutes. 1.25 grams of May-Greenwald's (Giemsa) stain (Mathison-Coleman, Norwood, Ohio) were then added and sonication continued for 15 more minutes at a No. 4 setting. The temperature of the mixture was elevated by sonic energy to approximately 40° to 50°. Four milliliters of the mixture were then removed for testing and the remaining mixture sonicated for another 15 minutes at the No. 5 setting (approximately 240 micron peak-to-peak excursion). Eight milliliters of water were added, followed by ten minutes sonication at a No. 5 setting which decreased the thickness of the suspension. The suspension was then broken into five milliliter aliquots contained in 13×100 millimeter test tubes. Each tube was sonicated five minutes at a No. 7 setting (approximately 340 microns peak-to-peak excursion) with an occasional dip in a beaker of water to keep the suspension from boiling and then centrifuged for ten minutes (2400 r.p.m., 12 inch rotor). The pH was 4.45 and was readjusted to 1.87 with one drop of 6N HCl followed by a three minute high power sonication (approximately 300 micron peak-to-peak excursion at 20 KHz) to form a violet-colored ink of May Greenwald's (Giemsa) stain-associated phospholipid vesicles.

Example II

The above procedure was modified to prepare a black ink. Five (5) grams of lecithin (as above) were added to 25 milliliters of distilled water in a roundbottomed flask which contained 20 milligrams L-ascorbic acid (sodium salt) and 20 milligrams 0.2% sodium azide. The mixture was dispersed by sonication (as above) at a No. 4 setting for ten minutes. Ten milliliters of H$_2$O and drops of 6N HCl were added which brought the pH from about 6.5 to below 2, followed by addition of 1.25 grams of Sudan Black B dye (Eastman Kodak). The suspension was sonicated for ten minutes at a No. 7 setting, and 15 minutes at a No. 5 setting with no cooling by a water bath. The suspension was then split in 5 ml aliquots in 13×100 mm test tubes and each sample sonicated for three minutes at a No. 7 setting. Samples were then centrifuged (2400 r.p.m., 12 inch rotor) for ten minutes to remove unincorporated Sudan Black B dye.

Example III

To a 20 ml sample of stock solution, 16 mg. L-ascorbic acid, 40 mg. sodium azide and two grams of the lipid phosphatidylcholine (Calbiochem, 98% pure) were added. The lipid was dispersed using sonication in a large tube (28×100 mm) for 5 minutes, using a sonicator as described in Examples I and II, at a No. 4 setting with cooling by a hot water bath. Only the bottom four centimeters of the microtrip were submerged. A suspension of Sudan Black B dye (Eastman Kodak), (2.5 g) and HCl (0.8 ml, 6N) in 8 mls of water was added to the resulting lipid suspension. The mixture was stirred using a vortex stirrer, and then dispersed by sonication on a No. 4 setting for 3 minutes with no cooling. The mixture was divided into aliquots in small (13×100 mm) test tubes and each tube was sonicated first at a No. 7 setting for 10 minutes and then at a No. 5 setting for 5 minutes with cooling by a hot (below boiling) water bath. Finally, the ink was centrifuged at 2500 r.p.m. for 50 minutes, and decanted.

Example IV 30 mg of dioctadecyldimethyl ammonium (DODAB) (Eastman Kodak) bromide and 15 mg of Sudan BB were added to 5 ml of water in a small tube (13×100 mm) and sonicated. (Sonicator 350, Heat System Ultrasonic, N.Y. set at 70 W.) The ink was then centrifuged until Sudan BB-associated dioctadecyldimethyl ammonium bromide vesicles were formed, approximately 40–800 nanometers in diameter.

Example V 30 mg of dihexadecyl phosphate and 3 mg of Sudan BB were added to 5 ml of water and sonicated as in Example IV followed by centrifugation for ten minutes. Formed thereby were dihexadecyl phosphate vesicles with which the lipid soluble dye, Sudan BB was associated.

CHARACTERIZATION OF VESICLE INK COMPOSITIONS

The viscosity of the vesicle ink compositions was measured using a Cannon Fenske Kinematic viscometer. The percentage of dye uptake was calculated by diluting the unincorporated dye into an organic solvent and measuring optical density with a Carey 14 spectrophotometer. The pH of the ink was determined using a conventional glass electrode pH meter. The test for waterfastness consisted in the comparison of the shape and optical density of the ink before and after water treatment (immersion in water for 10 minutes).

Functional testing of the ink compositions prepared as described above in Examples I and II was carried out using Radio Shack CGP-220 (Cannon) and Diablo (Sharp) ink-jet printers using piezo-electric drivers and a Hewlett Packard "Thinkjet ®" (bubblejet) printer. The ink composition prepared as described above in Example III was tested only on the Radio Shack ink-jet printer. The ink compositions of Examples IV and V were tested on a simulated ink-jet drop-on-demand printer located at Xerox Research Centre of Canada. Papers tested included clay coated inkjet paper as sold by Xerox, letterhead (high rag, rough surface), Strathmore bond, and photocopy quality paper.

Results

Examples I and II were subjected to optical density and functional testing only.

For Example III only, dye uptake into the ink was determined to be 6.05% dye by weight/ml of ink composition, which represents 68% dye uptake. Viscosity was determined to be 3.7 cps (measured against a water standard of 1). The final pH of this ink composition was 1.8, and the ink was of a suitable liquid consistency.

The optical density of the images using ink compositions of Examples I, II, and III were all within the desired range of 1.0 to 1.4. Ink compositions diluted with 20% water were found to jet satisfactorily. The images were not removed on immersion in water.

The vesicle ink jetted without clogging in all printers. Less expensive plain bond paper such as the photocopy quality paper, as well as coated specialty papers normally required with ink jet printers could be used with these inks. The observable ability of the vesicles to fix rapidly to all types of paper prevented any significant feathering. In addition, the ink absorbed and dried within 30–60 seconds. The printed image resisted smudging as determined by rubbing with the thumb under moderate pressure.

The inks of Examples IV and V imaged with enhanced resolution, improved feathering over the supplied commerical ink, and the image was not removed on exposure to water.

The ink composition of this invention can be applied in a number of ways using appropriate printing systems including flexographic, rotogravure presses or electronic devices such as ink jet or bubble jet printers. In addition, the ink can be applied by stamps (ink pads) or from rollers or belts to imprint on paper.

Although this invention has been described with reference to particular applications, the principles involved are susceptible of other applications which will be apparent to persons skilled in the art. The invention is, therefore, to be limited only as indicated by the scope of the claims appended hereto.

What is claimed is:

1. An aqueous ink composition comprising a dye soluble in the hydrocarbon bilayer of vesicles formed from surfactants selected from the group consisting of anionic, cationic, zwitterionic and nonionic molecules having a polar group and two nonpolar hydrocarbon moieties.

2. The composition according to claim 1 wherein said vesicles are of dihexadecyl phosphate.

3. The composition according to claim 1 wherein said vesicles are of dioctadecyl dimethyl ammonium bromide.

4. The composition according to claim 1 wherein said vesicles are of phospholipid.

5. The composition according to claim 1 wherein said vesicles are of diacyl glycerides and their ethoxylated derivatives.

6. The composition according to claim 1 wherein said vesicles are in the range of approximately 40 to 800 nanometers in diameter.

7. The composition according to claim 6 wherein said vesicles are in the range of approximately 100–400 nanometers.

8. The composition according to claim 4 wherein the phospholipid vesicles consist of partially purified phospholipid in the range of 70 to 100% purity.

9. The composition according to claim 4 wherein the phospholipid vesicles consist essentially of soybean L-α-lecithin.

10. The composition according to claim 1 wherein the dye is an oil soluble dye.

11. The composition according to claim 10 wherein the oil soluble dye is a lipid soluble dye.

12. The composition according to claim 1 wherein the proportion of the lipid soluble dye to surfactant is from about 1:1 to about 1:10 by weight.

13. The composition according to claim 1 wherein the water comprises from about 70 percent to about 95 percent by weight of the total ink composition.

14. The composition according to claim 1 wherein the vesicles and dye comprise from about 5 percent to about 30 percent by weight of the total ink composition.

15. The composition according to claim 1 wherein the dye comprises from about 1.0 percent to about 10 percent by weight of the vesicles.

16. The composition according to claim 1 wherein the surfactant comprises from about 5% to about 30% by weight of the total ink composition.

17. The composition according to claim 1 wherein the surfactant comprises from about 5% to about 20% by weight of the total ink composition.

18. The composition according to claim 10 wherein the lipid soluble dye is selected from the group consisting of Sudan Black B, Giemsa stain and Pylakrome.

19. A method for preparing an ink composition suitable for use in printing systems comprising the steps of:
    (a) suspending a surfactant and optionally, an antioxidant and a microbial inhibitor in water;
    (b) subjecting the suspension to a shear force sufficient to generate vesicles of desired size;
    (c) adding a lipid soluble dye to the sheared suspension;
    (d) adjusting the pH of the solution to enhance dye incorporation;
    (e) further subjecting said dye solution to shear force; and
    (f) centrifuging the sheared solution, thereby obtaining dye-associated vesicles.

20. The method according to claim 19 wherein said vesicles are of dihexadecyl phosphate.

21. The method according to claim 19 wherein said vesicles are of dioctadecyl dimethyl ammonium bromide.

22. The method according to claim 19 wherein said vesicles are of phospholipid.

23. The method according to claim 19 wherein said vesicles are of diacyl glycerides and their ethoxylated derivatives.

24. The method according to claim 19 wherein said vesicles are approximately 40 to 800 nanometers in diameter.

25. The method according to claim 24 wherein said vesicles are approximately 100 to 400 nanometers in diameter.

26. The method according to claim 19 wherein said surfactants are anionic, cationic, zwitterionic or nonionic molecules.

27. The method according to claim 22 wherein the phospholipid is partially purified phospholipid in the range of 70 to 100% purity.

28. The method according to claim 27 wherein the phospholipid is soybean L-α-lecithin.

29. The method according to claim 19 wherein about 5.0 grams to about 10 grams surfactant are suspended.

30. The method according to claim 19 wherein the lipid soluble dye is selected from the group consisting of Sudan Black B, Giemsa stain and Pylakrome.

31. The method according to claim 19 wherein about 0.5 grams to about 5.0 grams of lipid soluble dye are added.

32. The method according to claim 19 wherein the final pH of the composition is adjusted to within the range of about pH 1.5 to about 3.

33. The method according to claim 19 wherein the antioxidant is L-ascorbic acid.

34. The method according to claim 19 wherein the antioxidant is present in the amount of about 0% to about 0.4% by weight.

35. The method according to claim 19 wherein the microbial inhibiting compound is sodium azide.

36. The method according to claim 19 wherein the microbial inhibiting compound is present in the amount from about 0% to about 0.05%.

37. The composition of claim 16 in which said vesicles are approximately 40 to about 800 nanometers in diameter and said composition comprises from about 1.0 percent to about 10 percent of said dye and about 70 to about 95 percent water based on the weight of said vesicles.

38. The composition of claim 37 in which said vesicles are of phospholipid of 70 to 100 percent purity.

* * * * *